US012575878B2

(12) United States Patent
de la Rama et al.

(10) Patent No.: US 12,575,878 B2
(45) Date of Patent: Mar. 17, 2026

(54) MAPPING AND ABLATION CATHETER WITH MULTIPLE LOOP SEGMENTS

(71) Applicant: CRC EP, Inc., Lake Oswego, OR (US)

(72) Inventors: Alan de la Rama, Cerritos, CA (US);
Cary Hata, Irvine, CA (US)

(73) Assignee: CRC EP, Inc., Lake Oswego, OR (US)

( * ) Notice: Subject to any disclaimer, the term of this patent is extended or adjusted under 35 U.S.C. 154(b) by 513 days.

(21) Appl. No.: 17/608,067

(22) PCT Filed: Apr. 23, 2020

(86) PCT No.: PCT/EP2020/061275
§ 371 (c)(1),
(2) Date: Nov. 1, 2021

(87) PCT Pub. No.: WO2020/224972
PCT Pub. Date: Nov. 12, 2020

(65) Prior Publication Data
US 2022/0218412 A1     Jul. 14, 2022

Related U.S. Application Data

(60) Provisional application No. 62/844,143, filed on May 7, 2019.

(30) Foreign Application Priority Data

Nov. 15, 2019     (EP) ..................................... 19209312

(51) Int. Cl.
*A61B 18/14*          (2006.01)
*A61B 17/00*          (2006.01)
*A61B 18/00*          (2006.01)

(52) U.S. Cl.
CPC .... *A61B 18/1492* (2013.01); *A61B 2017/003* (2013.01); *A61B 2017/00867* (2013.01);
(Continued)

(58) Field of Classification Search
CPC .......... A61B 18/1492; A61B 2017/003; A61B 2017/00867; A61B 2018/0016;
(Continued)

(56) References Cited

U.S. PATENT DOCUMENTS 5,680,860 A  *  10/1997  Imran ................ A61B 18/1492
                                                    606/41
5,797,953 A  *  8/1998  Tekulve ........... A61B 17/12145
                                                    623/1.22
(Continued)

FOREIGN PATENT DOCUMENTS

EP          3023069 A1     5/2016
EP          3254635 A1     12/2017
(Continued)

OTHER PUBLICATIONS

International Search Report (PCT/ISA/210) and Written Opinion (PCT/ISA/237) mailed on Aug. 3, 2020, by the European Patent Office as the International Searching Authority for International Application No. PCT/EP2020/061275.
(Continued)

*Primary Examiner* — Daniel W Fowler
*Assistant Examiner* — Lindsay Regan Lancaster
(74) *Attorney, Agent, or Firm* — Buchanan Ingersoll & Rooney PC

(57)          ABSTRACT

A mapping and ablation catheter is presented. The mapping and ablation catheter comprising an elongated catheter shaft and an ablation portion being arranged at a distal end of the catheter shaft, wherein: the ablation portion comprises a plurality of loop segments; at least one first loop segment of the plurality of loop segments exhibits one or more ablation electrodes, the one or more ablation electrodes being configured for delivering energy to vascular tissue; the loop segments together form a three-dimensional spiral; and
(Continued)

respective diameters of the loop segments are such that each loop segment rests on a neighboring loop segment when the three-dimensional spiral is compressed. The plurality of loop segments comprises a stabilizer loop segment, which does not does not exhibit any electrodes, wherein the stabilizer loop segment is the most proximal loop segment of the plurality of loop segments.

14 Claims, 5 Drawing Sheets

(52) U.S. Cl.
CPC ................. *A61B 2018/0016* (2013.01); *A61B 2018/00357* (2013.01); *A61B 2018/00577* (2013.01); *A61B 2018/00839* (2013.01); *A61B 2018/1435* (2013.01); *A61B 2018/1467* (2013.01); *A61B 2018/1497* (2013.01); *A61B 2218/002* (2013.01)

(58) Field of Classification Search
CPC .......... A61B 2018/00357; A61B 2018/00577; A61B 2018/00839; A61B 2018/1435; A61B 2018/1467; A61B 2018/1497; A61B 2218/002; A61B 2018/00214; A61B 2018/00351; A61B 2018/00375; A61B 2018/1437
See application file for complete search history.

(56) References Cited

U.S. PATENT DOCUMENTS

| | | | |
|---|---|---|---|
| 6,666,853 B2 | 12/2003 | Chu et al. | |
| 7,101,368 B2 | 9/2006 | Lafontaine | |
| 7,309,325 B2 * | 12/2007 | Mulier | A61B 18/1477 |
| | | | 606/41 |
| 7,988,690 B2 * | 8/2011 | Chanduszko | A61B 17/0057 |
| | | | 606/49 |
| 8,540,704 B2 | 9/2013 | Melsky et al. | |
| 8,641,704 B2 | 2/2014 | Werneth et al. | |
| 9,352,134 B2 | 5/2016 | Levin et al. | |
| 9,717,559 B2 | 8/2017 | Ditter et al. | |
| 9,861,437 B2 | 1/2018 | Melsky et al. | |
| 2001/0007070 A1 * | 7/2001 | Stewart | A61B 18/1492 |
| | | | 606/41 |
| 2007/0162108 A1 * | 7/2007 | Carlson | A61M 25/09 |
| | | | 623/901 |
| 2011/0004087 A1 * | 1/2011 | Fish | A61B 5/6857 |
| | | | 29/592.1 |
| 2013/0006238 A1 * | 1/2013 | Ditter | A61B 18/1492 |
| | | | 606/41 |
| 2014/0309513 A1 * | 10/2014 | Fish | A61B 5/6857 |
| | | | 600/374 |
| 2015/0073515 A1 * | 3/2015 | Turovskiy | A61N 1/28 |
| | | | 607/101 |
| 2016/0143689 A1 * | 5/2016 | Ditter | A61B 18/1492 |
| | | | 606/46 |
| 2018/0311497 A1 * | 11/2018 | Viswanathan | A61N 1/0517 |
| 2019/0076179 A1 | 3/2019 | Babkin et al. | |

FOREIGN PATENT DOCUMENTS

| | | |
|---|---|---|
| WO | 02089687 A1 | 11/2002 |
| WO | 2016197186 A1 | 12/2016 |

OTHER PUBLICATIONS

Chinese Office Action for Chinese Patent Application No. 202080032777.X dated Feb. 29, 2024.

* cited by examiner

MAPPING AND ABLATION CATHETER WITH MULTIPLE LOOP SEGMENTS

CROSS-REFERENCE TO RELATED APPLICATIONS

This application is the United States national phase under 35 U.S.C. § 371 of PCT International Patent Application No. PCT/EP2020/061275, filed on Apr. 23, 2020, which claims the benefit of European Patent Application No. 19209312.8, filed on Nov. 15, 2019, and of U.S. Patent Application No. 62/844,143, filed on May 7, 2019, the disclosures of which are hereby incorporated by reference herein in their entireties.

TECHNICAL FIELD

The present invention relates to embodiments of a mapping and ablation catheter. In particular, the present invention relates to embodiments of a mapping and ablation catheter that may be used for pulmonary vein isolation (PVI), such as a multi-electrode irrigated radiofrequency (RF) ablation catheter.

BACKGROUND

It is known to use ablation catheters for PVI procedures in the therapy of atrial fibrillation (AF) patients. In such procedures, the pulmonary vein (PV) is electrically isolated from the left atrium by creating contiguous circumferential ablation lesions around the pulmonary vein ostium (PVO). Thus, irregular atrial contractions can be avoided by hindering undesired perturbing electrical signals generated within the PV from propagating into the left atrium.

Several types of AF ablation catheters are available including single point tip electrode catheters, circular multi-electrode loop catheters, and balloon-based ablation catheters using different energy sources. Examples include, a cryo-balloon catheter as described in U.S. Pat. No. 6,666,853 B2 and U.S. Pat. No. 7,101,368 B2; a laser balloon catheter as described in U.S. Pat. No. 8,540,704 B2 and U.S. Pat. No. 9,861,437 B2; an RF balloon catheter as described in U.S. Pat. No. 9,352,134 B2; an electrode array catheter as described in U.S. Pat. No. 8,641,704 B2; and an irrigated multi-electrode catheter as described in U.S. Pat. No. 9,717,559 B2.

European Publication No. 3 023 069 A1 relates to a multi-electrode, irrigated luminal catheter with a soft distal tip for mapping and ablating a tubular region. Particularly disclosed is a catheter tip with a soft distal loop and a stiffer proximal loop, the proximal loop having ablation ring electrodes, and the distal loop having ring electrodes for sensing electrical potentials.

U.S. Publication No. 2001/007070 and WO Publication No. 02/089687 A1 each describe a catheter with a helical distal portion and an ablation portion formed along the helix.

The known ablation catheters have several drawbacks.

For example, if a single irrigated tip is used to do a point-by-point ablation, this method is slow and tedious, and requires a skilled electrophysiology (EP) physician. Also, with a single irrigated tip, ablation lesion gaps are quite problematic and may require redo procedures.

One-shot balloon catheters can be rather non-compliant and sometimes slip out of the PVO. Moreover, such catheters require a relatively large French size delivery sheath.

Multi-electrodes on a single circular loop structure may have tissue contact challenges because the single loop is not able to accommodate various PVO shapes and size due to the inherent variability in the human anatomy between individuals.

The present disclosure is directed toward overcoming one or more of the above-mentioned problems, though not necessarily limited to embodiments that do.

SUMMARY

It is an object of the present invention to provide an improved ablation catheter for PVI.

At least this object is achieved by a catheter, particularly an ablation catheter, comprising an elongated catheter shaft and an ablation portion being arranged at a distal end of the catheter shaft, wherein: the ablation portion comprises a plurality of loop segments (i.e., at least two loop segments); at least one first loop segment of the plurality of loop segments exhibits one or more ablation electrodes, the one or more ablation electrodes being configured for delivering energy to vascular tissue; the loop segments together form a three-dimensional spiral; and respective diameters of the loop segments are such that each loop segment rests on a neighboring loop segment when the three-dimensional spiral is compressed. In particular, it may be provided that each loop segment may rest on a neighboring loop segment along its entire circumference when the three-dimensional spiral is compressed.

The ablation catheter may be primarily configured for ablation in the PVO as well as other atrial regions of the human heart.

The three-dimensional spiral formed by the plurality of loop segments may be a graduation of a helix with variable radiuses, wherein the ablation electrodes may be disposed circumferentially on the first loop segment. Hence, for example, the ablation portion may exhibit an essentially cyclone-shaped tip formed of the loop segments, which will also be referred to as helical loop segments in the following.

Due to the cyclone-shaped or helical structure and the flexibility of the loop segments, the ablation portion may better conform to the differing shapes of the PVO as compared to that of a single circular loop type ablation catheter. Thus, a good tissue contact may be achieved, which may result in a more targeted energy delivery and, potentially, shorter ablation times for creating contiguous lesions. In other words, the proposed ablation catheter may be particularly suitable for a High-Power/Short Duration ablation approach, which has become generally very appealing to EP physicians in recent years.

Further, the plurality of loop segments may comprise a stabilizer loop segment, which does not exhibit any electrode, wherein the stabilizer loop segment is the most proximal loop segment of the plurality of loop segments. The stabilizer loop segment may also be referred to as a rear loop segment.

The rear loop segment may be configured to add lateral stability and structural support to the distal loop assembly when it is engaged in the pulmonary veins, such that the ablation electrodes may act on the PVO or other atrial region of the heart during the course of the ablation procedure. Since the stabilizer loop segment has no ablation electrodes, its shape and arrangement may be optimized for a stabilizing function, in particular during a PVI procedure when the ablation portion engages with the PV in the vicinity of the PVO.

For example, in an embodiment, a diameter of the stabilizer loop segment is smaller than a diameter of a neighboring loop segment, i.e., of a neighboring loop section being arranged distal from the stabilizer loop segment. As a result, the ablation portion as a whole (including the stabilizer loop segment) may exhibit a barrel shaped contour or at least a semi-barrel shaped contour.

In an embodiment, also a second loop segment of the plurality of loop segments comprises a plurality of ablation electrodes. For example, the second loop segment and the first loop segment, each comprising several ablation electrodes, may be neighboring loop segments. In particular, the ablation electrodes of the second loop segment may be arranged in a staggered manner with respect to the ablation electrodes of the first loop segment.

With current PVI procedures being targeted more in the PV antrum and also some non-PV AF trigger sites in the atrium, the two helical ablation loop segments, each of which has ablation electrodes, allow a broader or wider ablation zone, somewhat comparable to the effect of a balloon ablation catheter.

To achieve this without adding too many more ablation electrodes (which might render it more difficult to create contiguous lesions), it may be advantageous to use relatively long ablation electrodes. For example, a length of the ablation electrodes may be equal to or greater than 4.0 mm.

In a preferred variant, the ablation electrodes may be sleeve-shaped or tubular. For example, a diameter of such a sleeve-shaped or tubular ablation electrode may be equal to or greater than 2.0 mm. Further, as mentioned above, a length of the sleeve-shaped or tubular ablation electrode may be equal to or greater than 4.0 mm.

As a suitable material, the ablation electrodes may comprise, for example, at least one of gold and a platinum/iridium alloy.

In accordance with an embodiment, the ablation catheter is configured for delivering an electrical RF signal to vascular tissue via the ablation electrodes. In other words, the ablation catheter may be configured for carrying out RF ablation. Currently, RF is still the preferred energy over other energies due to its long history of use in PVI.

For example, the ablation catheter may be configured for being connected to a multi-channel RF generator which is configured for delivering RF energy and for transmitting electrogram signals for PVI procedures in AF patients.

In other embodiments, the proposed spiral-shaped architecture of the ablation portion may be applied to an ablation catheter utilizing energy sources other than RF, such as electroporation, pulsed field ablation, or cryo-ablation.

Preferably, the ablation electrodes are irrigated ablation electrodes, such as saline irrigated ablation electrodes. To this end, the ablation electrodes can have vents and/or plurality of micro-holes or pores and to facilitate delivery of irrigation fluid.

Thus, the ablation electrodes may be cooled by an irrigation fluid during operation. Further, a conductive irrigation liquid may support the delivery of electrical energy (such as RF signals) to the vascular tissue, thereby allowing for the targeted creation of contiguous lesions.

For example, when the ablation electrodes are sleeve-shaped or tubular, a tubular wall of each ablation electrode may comprise helical irrigation vents or cuts. Thus, a throughput of the irrigation may be spread uniformly along the length of the ablation electrode, particularly for improved cooling. An additional advantage of the helical vents or cuts particularly for electrode with longer length (4.0 mm or greater) is that the electrode becomes more flexible and therefore be more conforming to tissue contact at the PVOs in contrast to a solid ring electrode.

For example, a lumen for saline irrigation delivery provided in the loop segments can have various stiffness and cross-sectional shapes to deliver saline irrigation to all ablation electrodes homogeneously.

Furthermore, some or all of the ablation electrodes may comprise one or more temperature sensors to monitor an electrode temperature, and provide feedback to, e.g., a multi-channel RF generator for controlling ablation parameters, such as power and irrigation flow.

It is also within the scope of the present invention that the ablation portion may comprise a plurality of mapping electrodes, the mapping electrodes being configured for receiving electrical signals from vascular tissue. This may enable mapping and ablation with a single ablation catheter for PVI as well as ablating some non-PV triggers for AF patients.

For example, in an embodiment, a third loop segment of the plurality of loop segments may exhibit a plurality of mapping electrodes. Additionally or alternatively, mapping electrodes may also be arranged in addition to the ablation electrodes on the first loop segment and/or, where applicable, on the second loop segment as mentioned above. A plurality of mapping electrodes can also be incorporated distal to the plurality of ablation electrodes, or medially within two ablation electrodes. Furthermore, the third loop segment may comprise ablation electrodes in addition to or instead of the mapping electrodes.

In an advantageous embodiment, the ablation portion, and in particular the loop segments, comprise a shape memory material. Preferably, the shape memory material is a super-elastic material (such as a super-elastic alloy), which is to say that the material is elastic and has a shape memory property. For example, nitinol is a biocompatible super-elastic alloy that is suitable for the present purpose.

In one variant, the ablation portion, and in particular the loop segments, may comprise an inner support element, such as an inner support wire, having such a shape memory or super-elastic property. The inner support wire may be a nitinol wire, for example. The shape memory support wire can have various stiffness and cross-sectional shapes.

In an embodiment, the ablation catheter further comprises a steerable delivery sheath. Thus, in operation, a position of the ablation portion may be easily adjusted at the target visceral tissue until the contact of each ablation electrode is satisfied.

Advantageously, in some embodiments, the proposed spiral-shaped configuration of the ablation portion may require a smaller sized transseptal sheath than those used with existing balloon ablation catheters.

In another embodiment, the catheter, particularly the ablation catheter, further comprises at least one or two pulling wire(s) from the handle in the catheter proximal end and attached to the distal section of the main shaft to enable uni- or bi-directional deflection of the distal loop segments. Additional pulling wire can be included to compress or adjust the diameters of the loop segments. These catheter features allow further adjustment capabilities to improve the alignment of the loop segments within the PVO.

The catheter, particularly the ablation catheter, having a multi-ablation electrode configuration disclosed herein addresses the drawbacks of the available approaches mentioned above. Further, the spiral architecture of the ablation portion, preferably in combination with irrigated flexible ablation electrodes, addresses tissue contact challenges.

All aspects and features of the embodiments described above and in the following can be combined with each other unless explicitly stated otherwise. Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein, FIG. 1 schematically and exemplarily illustrates a distal portion of an ablation catheter in accordance with one or more embodiments.

DETAILED DESCRIPTION

Figure 1:
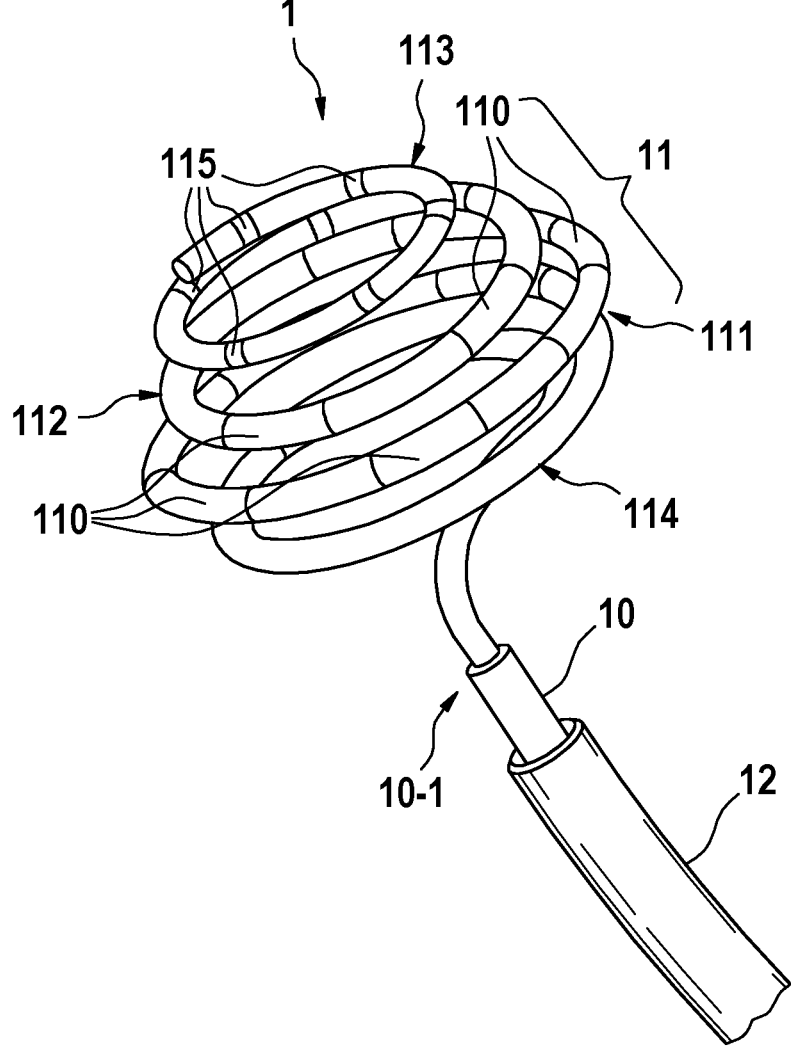

FIG. 1 schematically and exemplarily illustrates a distal portion of an ablation catheter 1 in accordance with one or more embodiments. The catheter 1 has an elongated circular catheter shaft 10, which may comprise a handle at a proximal end (not illustrated) to manipulate the deflections of the depicted distal end 10-1 of the catheter shaft.

Arranged at the illustrated distal end 10-1 of the catheter shaft 10 is an ablation portion 11, which comprises a plurality of compressible loop segments 111, 112, 113, 114. Each of a first loop segment 111 and a neighboring second loop segment 112 exhibits several ablation electrodes 110, which are configured for delivering energy to vascular tissue. In particular, the ablation catheter 1 may be configured for delivering an electrical RF signal to vascular tissue via the ablation electrodes 110. For example, the ablation electrodes 110 may consist of or comprise gold and/or a platinum/iridium alloy.

In the exemplary embodiment illustrated in FIG. 1, the ablation electrodes 110 of the second loop segment 112 are arranged in a staggered manner with respect to the ablation electrodes 110 of the first loop segment 111.

In addition, a third loop segment 113 is provided, wherein the third loop segment 113 is the most distal loop segment 113 of the plurality of loop segments 111, 112, 113, 114. In accordance with the present exemplary embodiment, the third loop segment 113 may therefore also be referred to as a front loop segment 113. The third loop segment exhibits a plurality of mapping electrodes 115, which are configured for receiving electrical signals from vascular tissue.

Furthermore, the plurality of loop segments 111, 112, 113, 114 comprises a stabilizer loop segment 114, which does not exhibit any electrodes. The stabilizer loop segment 114 is the most proximal loop segment of the plurality of loop segments 111, 112, 113, 114 and may therefore also be referred to as the rear loop segment 114.

Together, the loop segments 111, 112, 113, 114 form a (compressible) three-dimensional spiral, which features a cyclone-shaped tip portion. It should be noted that respective diameters of the loop segments 111, 112, 113, 114 are such that each loop segment 111, 112, 113, 114 rests on a neighboring loop segment 111, 112, 113, 114 along its entire circumference when the three-dimensional spiral is compressed. This is more clearly depicted in FIG. 3 and will be further explained in the description of FIG. 3 below.

Figure 3:
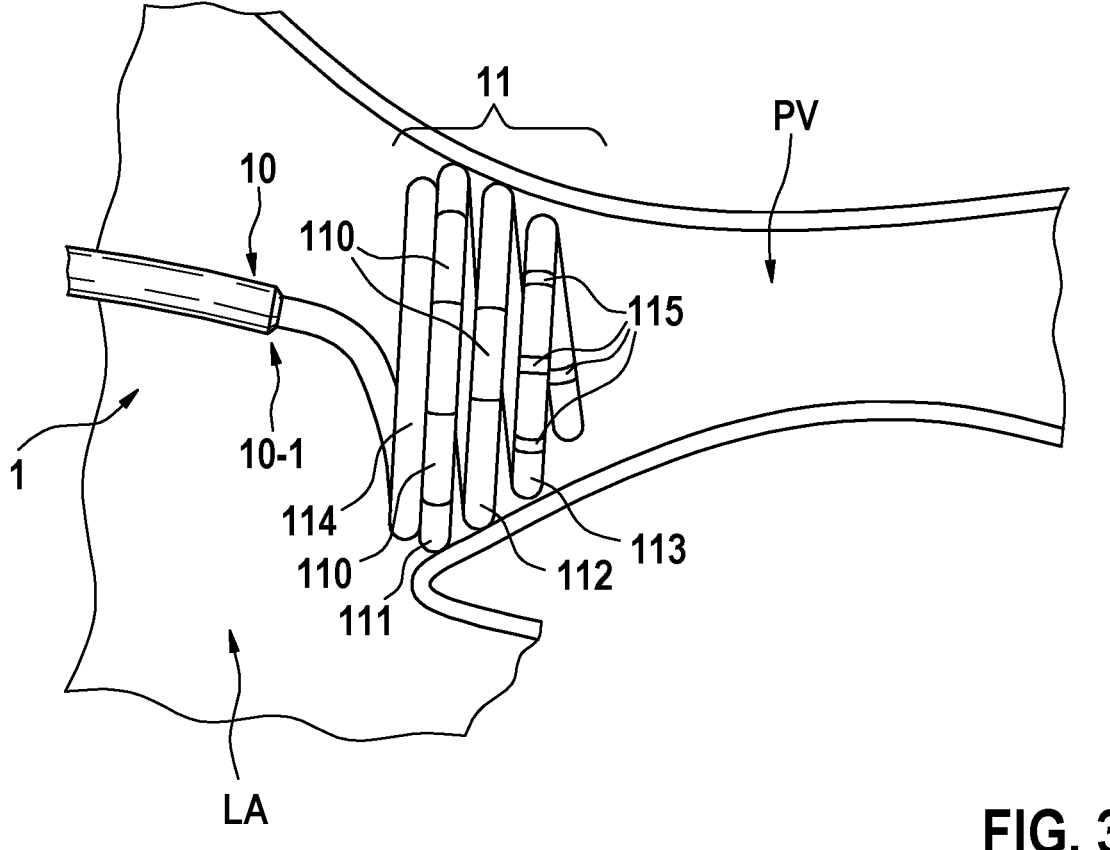
FIG. 3 schematically and exemplarily illustrates a distal portion of an ablation catheter located on the pulmonary vein ostium.

As can be seen in both FIG. 1 and FIG. 3, a diameter of the stabilizer loop segment 114 is smaller than a diameter of a neighboring first loop segment 111. In combination with the cyclone-shaped arrangement of the first, second and third loops 111, 112, 113 (having decreasing diameters in a direction from proximal to distal) this results in an essentially barrel-shaped contour of the ablation portion.

The loop segments 111, 112, 113, 114 may comprise a shape memory material, for example, in the form of an inner structural support wire (not illustrated) having a shape memory property. For example, a nitinol wire may be provided as an inner structural support wire. In particular, the loop segments 111, 112, 113, 114 may have super-elastic properties.

Thus, the ablation portion 11 may be brought from a biased configuration (e.g., as depicted in FIG. 1) in a different, constrained configuration, and vice versa. For example, for the purpose of delivery to a target region in the human body by means of a (fixed or steerable) delivery sheath 12, which may also be referred to as an introducer sheath 12, the ablation portion 11 may be constrained into an essentially elongate shape. At the target position, upon exiting a distal end of the introducer sheath 12, the ablation portion 11 may then recoil to its original (biased) shape.

Figure 2:
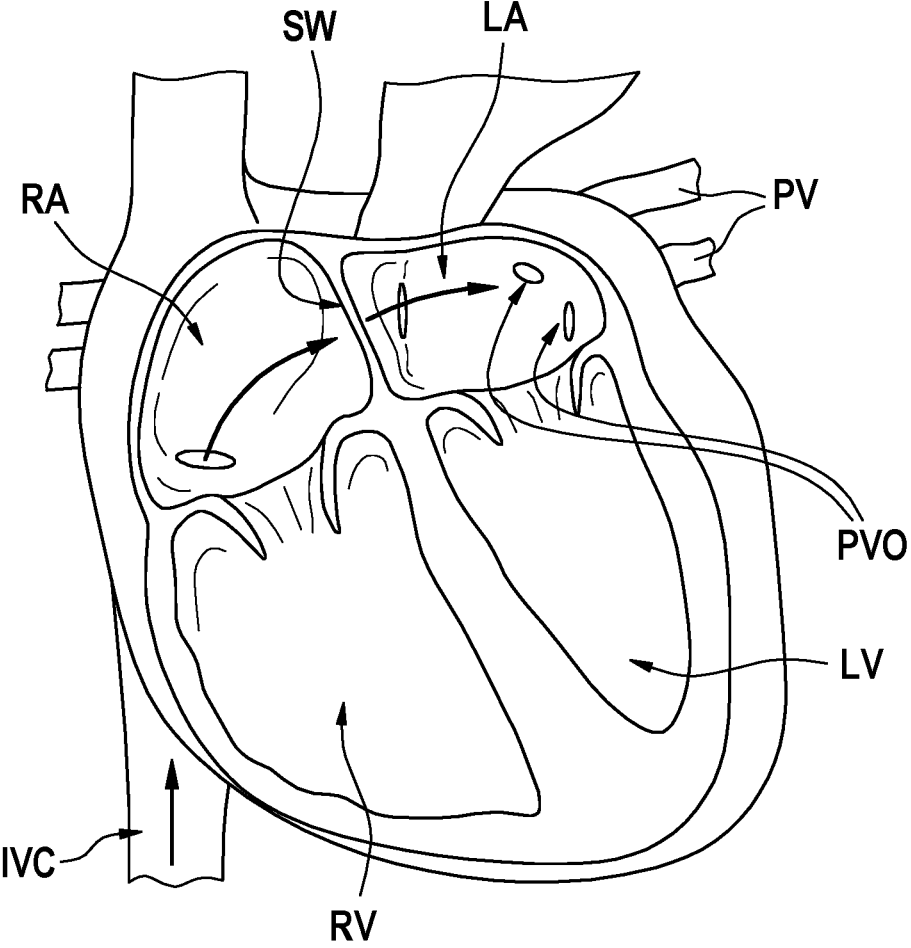
FIG. 2 schematically and exemplarily illustrates a delivery path for an ablation catheter leading to a pulmonary vein ostium of a human heart.

FIG. 2 schematically and exemplarily illustrates a delivery path for an ablation catheter 1 leading to a pulmonary vein ostium PVO of a human heart. For orientation, the inferior vena cava IVC, the right atrium RA, the right ventricle RV, the left atrium LA, the left ventricle LV, as well as pulmonary veins PV, each with a pulmonary vein ostium PVO, are shown. The large white arrows indicate a delivery path passing through the inferior vena cava IVC, the right atrium RA, transseptally through the septal wall SW, and the left atrium LA, finally leading to the region of a pulmonary vein ostium PVO.

FIG. 3 schematically and exemplarily illustrates a distal portion of the ablation catheter 1 located on a pulmonary vein ostium PVO. As illustrated, the spiral-shaped ablation portion 11 may be placed at the antrum of the pulmonary veins PV to achieve pulmonary vein isolation PVI ablation. The distal end 10-1 of the catheter shaft 10 and/or the steerable sheath 12 can be deflected to ensure the ablation portion 11 is properly aligned with the opening angle of the pulmonary vein ostium PVO. For example, the positioning of the ablation portion 11 may be adjusted until the contact for each ablation electrode 110 and/or mapping electrode 115 is satisfied. If needed, the steerable sheath 12 can be used to gently push the ablation portion 11 to maintain stability.

FIG. 3 shows a compressed state of the ablation portion 11, wherein each loop segment 111, 112, 113, 114 rests on a neighboring loop segment 111, 112, 113, 114 along its entire circumference. In particular, the rear loop segment 114 provides lateral stability and structural support to the distal loop assembly 111, 112, 113, 114.

Once the ablation portion is in a suitable position, ablation can be performed through the ablation electrodes 110 simultaneously, sequentially, or individually in a unipolar fashion, or in a bipolar mode between adjacent ablation electrodes 110 within the same loop 111, 112 or across the loop 111,

112. During the ablation the physician can observe the reduction of PV potentials with the mapping electrodes 115 and/or ablation electrodes 110.

Figure 4:
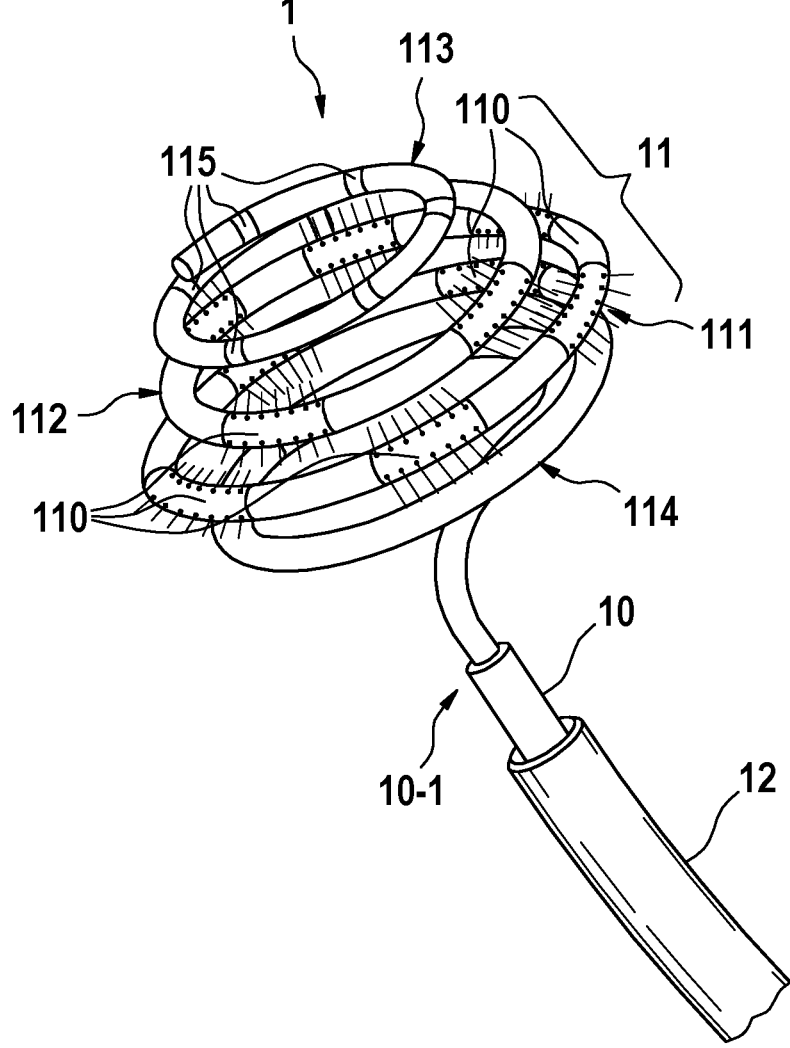
FIG. 4 schematically and exemplarily illustrates a distal portion of an ablation catheter comprising irrigated ablation electrodes in accordance with one or more embodiments.

FIG. 4 schematically and exemplarily illustrates a distal portion of an ablation catheter 1 comprising irrigated ablation electrodes 110 in accordance with one or more embodiments. In particular, FIG. 4 shows an irrigation fluid, such as saline irrigation fluid, being irrigated through irrigation vents and/or a plurality of micro-holes or pores provided in the ablation electrodes 110.

Figure 5:
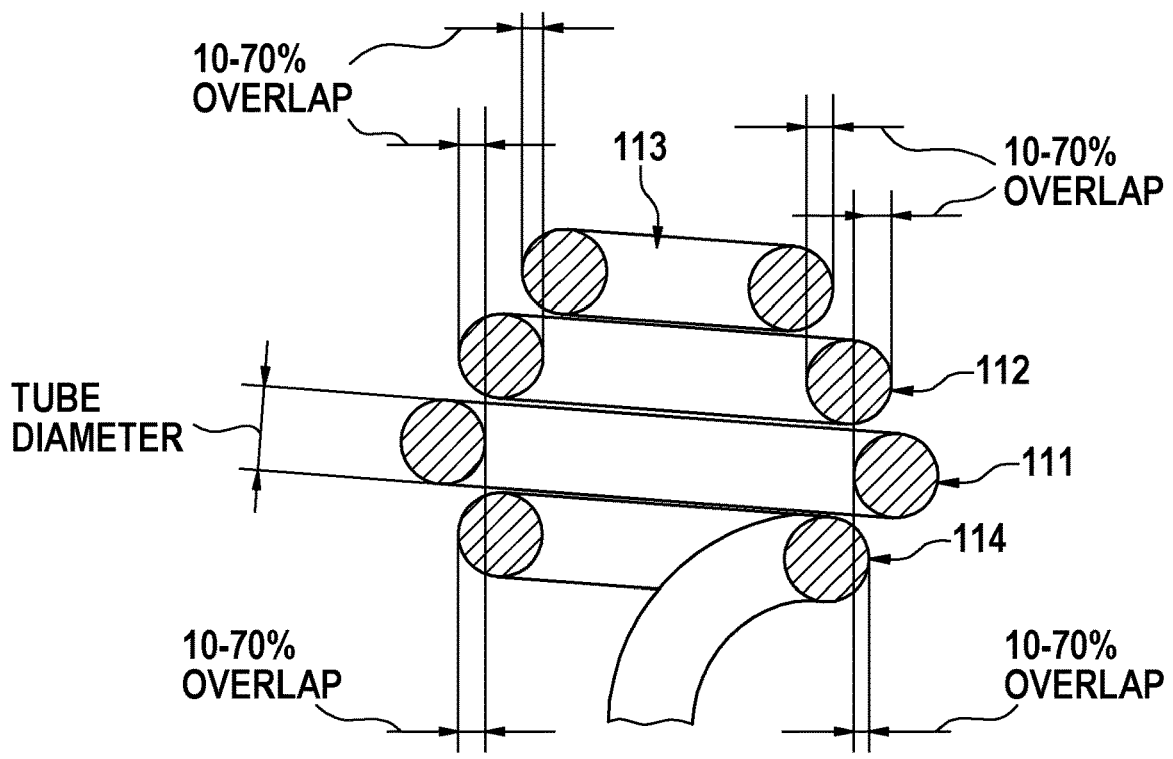
FIG. 5 illustrates a cross-sectional view of the distal portion as shown in FIGS. 3 and 4.

FIG. 5 shows a cross-sectional view of the distal portion as shown in FIG. 3, wherein particularly a 10-70% overlap of the tube or French diameter from one loop to the adjacent loop is illustrated. As shown in FIG. 3, each loop segment 111, 112, 113, 114 rests on an adjacent loop along its entire circumference, the tube or French diameter of loop segment 114 (referred to as rear loop segment) overlaps the adjacent tube diameter of loop 111 by 10-70%. The loop diameter of loop segment 114 is undersized to the loop diameter of the loop segment 111. The same can be said for loop segment 112 which is undersize in loop diameter of adjacent loop segment 111. Likewise, loop segment 113 is undersize to loop segment 112.

Figure 6:
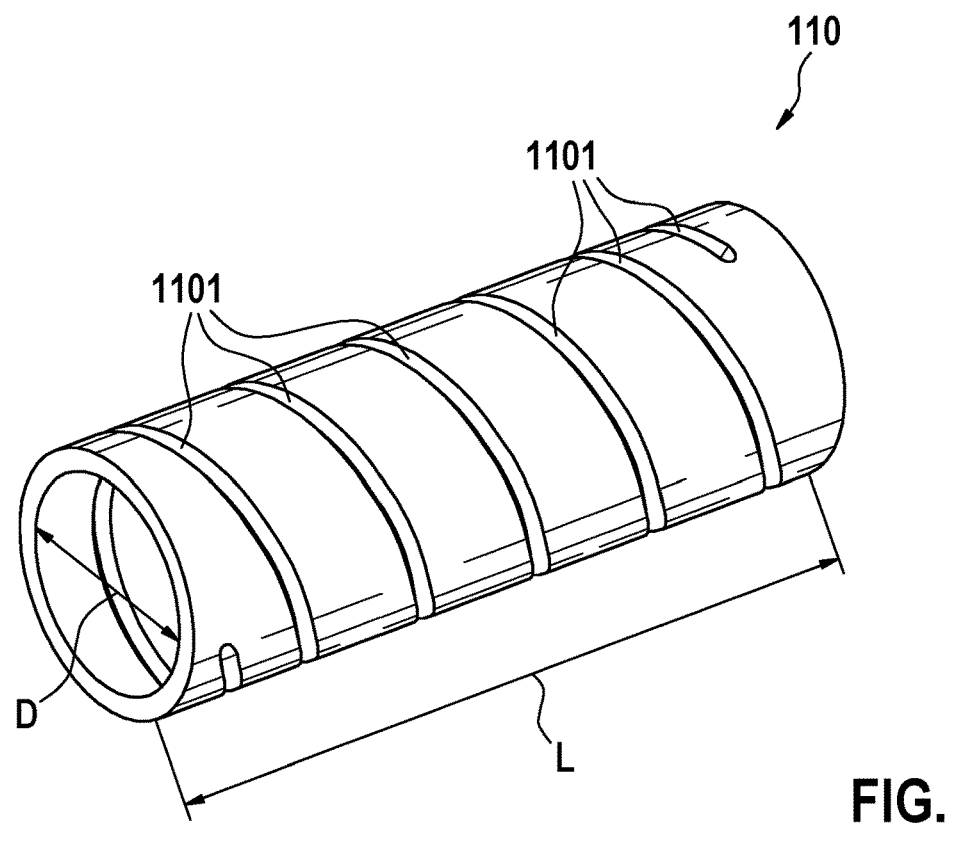
FIG. 6 schematically and exemplarily illustrates a sleeve-shaped ablation electrode of an ablation catheter in accordance with one or more embodiments.

FIG. 6 schematically and exemplarily illustrates an ablation electrode 110 of an ablation catheter 1 in accordance with one or more embodiments. The ablation electrode 110 is essentially sleeve-shaped or tubular.

A diameter D of such a sleeve-shaped or tubular ablation electrode 110 may be equal to or greater than 2.0 mm. A length L of the sleeve-shaped or tubular ablation electrode 110 may be equal to or greater than 4.0 mm.

The tubular wall of the ablation electrode 110 comprises helical irrigation vents or cuts 1101. Thus, a throughput of the irrigation is spread uniformly along the length L of the ablation electrode 110 with a plurality of micro-protrusion cuts 1102 as vent spacers.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Ablation catheter
10 Catheter shaft
10-1 Distal end of the catheter shaft
11 Ablation portion
110 Ablation electrode
1101 Irrigation vents
111 First loop segment
112 Second loop segment
113 Third loop segment
114 Stabilizer loop segment
115 Mapping electrode
12 Delivery sheath
D Diameter of the ablation electrode
IVC Inferior vena cava
L Length of the ablation electrode
LA Left atrium LV Left ventricle
PV Pulmonary vein
PVO Pulmonary vein ostium
RA Right atrium
RV Right ventricle
SW Septal wall

The invention claimed is:

1. An ablation catheter, comprising an elongated catheter shaft and an ablation portion being arranged at a distal end of the catheter shaft, wherein:

the ablation portion comprises a plurality of loop segments;

at least one first loop segment of the plurality of loop segments exhibits one or more ablation electrodes disposed circumferentially on the at least one first loop segment, the one or more ablation electrodes being configured for delivering energy to vascular tissue;

each loop segment has a diameter that differs from a diameter of another loop segment such that the loop segments together form a three-dimensional spiral;

respective diameters of the loop segments are such that each loop segment rests on a neighboring loop segment along its entire circumference when the three-dimensional spiral is compressed in an axial direction of the three-dimensional spiral so that the diameter of each loop segment overlaps an adjacent tube diameter of an adjacent loop segment by 10-70%;

wherein the three-dimensional spiral formed by the plurality of loop segments is a graduation with a helix with variable radiuses, and, the plurality of loop segments comprise a stabilizer loop segment, which does not exhibit any electrodes along a 360° extent of the stabilizer loop segment, wherein the stabilizer loop segment is the most proximal loop segment of the plurality of loop segments.

2. The ablation catheter according to claim 1, wherein a diameter of the stabilizer loop segment is smaller than a diameter of a neighboring loop segment.

3. The ablation catheter according to claim 1, wherein the ablation portion comprises a plurality of mapping electrodes, the mapping electrodes being configured for receiving electrical signals from vascular tissue.

4. The ablation catheter according to claim 1, wherein a second loop segment of the plurality of loop segments comprises a plurality of ablation electrodes and/or a plurality of mapping electrodes.

5. The ablation catheter according to claim 4, wherein the ablation electrodes of the second loop segment are arranged in a staggered manner with respect to the ablation electrodes of the first loop segment.

6. The ablation catheter according to claim 1, wherein a third loop segment of the plurality of loop segments exhibits the plurality of mapping electrodes.

7. The ablation catheter according to claim 1, wherein the ablation catheter is configured for delivering energy, particularly an electrical radiofrequency signal, to vascular tissue via the ablation electrodes.

8. The ablation catheter according to claim 1, wherein the ablation electrodes are irrigated ablation electrodes comprising helical irrigation vents or cuts.

9. The ablation catheter according to claim 1, wherein the ablation electrodes are sleeve-shaped.

10. The ablation catheter according to claim 1, wherein a material of the ablation electrodes comprises at least one of gold and a platinum/iridium alloy.

11. The ablation catheter according to claim 1, wherein the ablation portion comprises a shape memory material.

12. The ablation catheter according to claim 11, wherein the ablation portion comprises an inner support element having a shape memory property.

13. The ablation catheter according to claim 1, wherein the ablation catheter comprises a steerable delivery sheath.

14. The ablation catheter according to claim 1, wherein the stabilizer loop segment provides lateral stability and structural support for the plurality of loop segments.

* * * * *